United States Patent [19]

Lind

[11] 4,038,250

[45] July 26, 1977

[54] LIGHT PROTECTING AGENTS

[75] Inventor: Hanns Lind, Basel, Switzerland

[73] Assignee: Ciba-Geigy Corporation, Ardsley, N.Y.

[21] Appl. No.: 571,142

[22] Filed: Apr. 24, 1975

Related U.S. Application Data

[63] Continuation of Ser. No. 174,951, Aug. 25, 1971, abandoned.

[51] Int. Cl.$^2$ .............................................. C07C 69/76
[52] U.S. Cl. ......................... 260/45.85 B; 260/473 S
[58] Field of Search ......................... 260/473 S, 45.85

[56] References Cited

U.S. PATENT DOCUMENTS

| 3,502,613 | 5/1970 | Berger | 260/473 S |
|---|---|---|---|
| 3,843,595 | 10/1974 | Mathis et al. | 260/473 S |

*Primary Examiner*—Paul J. Killos
*Attorney, Agent, or Firm*—Nestor W. Shust; C. W. Vanecek

[57] ABSTRACT

New substituted p-hydroxybenzoic acid phenyl esters are light protecting agents for polymers. They are prepared by acylation of a corrsponding phenol with an appropriate acid chloride.

12 Claims, No Drawings

LIGHT PROTECTING AGENTS

This is a continuation of application Ser. No. 174,951 filed on Aug. 25, 1971, now abandoned.

The subject of the invention are new 4-hydroxybenzoic acid aryl esters, their use for protecting lightsensitive polymers, especially polyolefines, and, as an industrial product, the organic material protected with their aid against the harmful influence of light.

It is known to employ esters of 3,5-dialkyl-4-hydroxybenzoic acids as light protection agents for organic polymers. The aryl esters of this previously known class of light protection agents are distinguished by high activity, for example in polyolefines, but particularly in these substrates show the disadvantage that they cause a yellowing of the polymeric substrate in practical use. Furthermore, it is particularly the most active compounds of this series which show inadequate compatibility in certain forms of application, which causes a technically undesirable sweating-out from the polymer or a clouding thereof. Alkyl esters of 3,5-dialkyl-4-hydroxybenzoic acids show the disadvantage of yellowing of the polymer to a lesser extent and are also more compatible than the aryl esters, but show a distinctly lower light protection action than the latter.

It has now been found, surprisingly, that compounds of the formula I

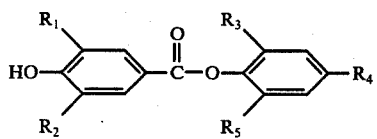

in which $R_1$ denotes alkyl with 1 – 5 carbon atoms, cycloalkyl with 5 – 8 carbon atoms or aralkyl with 7 – 9 carbon atoms, $R_2$ denotes α-branched alkyl with 3 – 8 carbon atoms, cycloalkyl with 5 – 8 carbon atoms or α-aralkyl with 7 – 9 carbon atoms, $R_3$ and $R_5$ independently of one another denote alkyl with 1 – 8 carbon atoms, cycloalkyl with 5 – 8 carbon atoms, aralkyl with 7 – 9 carbon atoms or phenyl, and $R_4$ denotes hydrogen, alkyl with 1 – 18 carbon atoms, cycloalkyl with 5 – 8 carbon atoms, aralkyl with 7 – 9 carbon atoms or phenyl, are excellent light protection agents for light-sensitive polymers, such as polyolefines.

The compounds of the formula I show the advantage, over the previously known aryl esters of 3,5-dialkyl-4-hydroxybenzoic acids, that in practical use they do not cause any yellowing of the polymeric substrates and that they are furthermore substantially more compatible. As compared to the previously known alkyl esters of 3,5-dialkyl-4-hydroxybenzoic acids, the compounds of the formula I show a significantly better light protection action. In other words, the compounds according to the invention surprisingly show the technically desired combination of excellent light protection action, compatibility, and stability of colour of the polymers stabilised therewith.

If $R_1$, $R_2$, $R_3$, $R_4$ or $R_5$ in formula I denote alkyl, then these can for example be, within the limits of the carbon atoms specified in the formula, methyl, ethyl, iso-propyl, sec.-butyl, tert.-butyl, sec.-amyl, tert.-amyl, tert.-hexyl, iso-octyl, tert.-octyl, sec.-nonyl, tert.-nonyl, sec.-dodecyl, tert.-dodecyl, sec.-tetradecyl or sec.-hexadecyl.

$R_1$, $R_3$, $R_4$ and $R_5$ can furthermore, within the limits of the carbon atoms specified under formula I, denote n-propyl, n-butyl, n-pentyl, n-hexyl, n-heptyl, n-octal, n-nonyl, n-dodecyl or n-octadecyl.

If $R_1$, $R_2$, $R_3$, $R_4$ or $R_5$ is cycloalkyl, this can be the cyclopentyl, cyclohexyl or the cyclooctyl radical.

If $R_1$, $R_2$, $R_3$, $R_4$ or $R_5$ is aralkyl, it can for example be benzyl, α-methylbenzyl or α,α-dimethylbenzyl.

A particular group of compounds of the formula I are those in which $R_1$ denotes alkyl with 1 to 5, preferably 1 to 4, carbon atoms and $R_2$ denotes alkyl with 3 to 8, preferably 3 and 4, carbon atoms, the number of carbon atoms in $R_1$ and $R_2$ not exceeding 10, $R_3$ and $R_5$ independently of one another denote alkyl with 1 to 8, preferably 1 to 4, carbon atoms, cycloalkyl with 6 to 8 carbon atoms, aralkyl with 7 or 8 carbon atoms or phenyl, and $R_4$ denotes hydrogen, alkyl with 1 – 12 carbon atoms, cycloalkyl with 6 – 8 carbon atoms, preferably cyclohexyl, aralkyl with 7 – 8 carbon atoms, or phenyl.

Particularly preferred compounds of the formula I are those in which $R_1$ denotes methyl, iso-propyl, sec.-butyl or tert.-butyl, $R_2$ denotes iso-propyl, sec.-butyl or tert.-butyl, $R_3$ and $R_5$ independently of one another denote methyl, iso-propyl, sec.-butyl, tert.-butyl, sec.-amyl, tert.-amyl, tert.-hexyl, tert.-octyl, cyclohexyl or α-methylbenzyl and $R_4$ denotes hydrogen, methyl, iso-propyl, sec.-butyl, tert.-butyl, sec.-amyl, tert.-amyl, tert.-hexyl, tert.-octyl, sec.-nonyl, tert.-dodecyl, cyclohexyl or α-methylbenzyl.

Examples of such compounds of the formula I which are particularly preferred according to the invention are:

3,5-di-tert.-Butyl-4-hydroxybenzoic acid 2'-methyl-4',6'-di-sec.-butylphenyl ester 3,5-di-tert.-Butyl-4-hydroxybenzoic acid 2'-methyl-4',6'-di-tert.-butylphenyl ester 3,5-di-tert.-Butyl-4-hydroxybenzoic acid 2'-methyl-4',6'-di-tert.-amylphenyl ester 3,5-di-tert.-Butyl-4-hydroxybenzoic acid 2',6'-di-sec.-butyl-4'-methylphenyl ester 3,5-di-tert.-Butyl-4-hydroxybenzoic acid 2',4'-di-methyl-6'-tert.-butylphenyl ester 3,5-di-tert.-Butyl-4-hydroxybenzoic acid 2',4'-di-methyl-6'-tert.-amylphenyl ester 3,5-di-tert.-Butyl-4-hydroxybenzoic acid 2',4'-6'-tri-isopropylphenyl ester 3,5-di-tert.-Butyl-4-hydroxybenzoic acid 2',4',6'-tri-sec.-butylphenyl ester 3,5-di-tert.-Butyl-4-hydroxybenzoic acid 2',4',6'-tri-tert.-butylphenyl ester 3,5-di-tert.-Butyl-4-hydroxybenzoic acid 2',6'-di-sec.-butyl4'-tert.-butylphenyl ester.

The compounds of the formula I protect organic polymers against degradation, such as, for example, polystyrene, polyvinyl chloride, polyvinylidene chloride, polyvinyl acetate, polyvinyl acetals, polyacetals, polyacrylates, polyisobutylene, polyisoprene and polybutadiene, and preferably polyolefines, such as high pressure and low pressure polyethylene, which can optionally also be crosslinked, α-olefine polymers such as, for example, polypropylene, polybutene-1, polymethylbutene-1 and polymethylpentene-1 in their tactic and atactic forms, copolymers of the monomers on which the homopolymers mentioned are based, such as, for example, ethylene-vinyl acetate copolymers, styrene-acrylonitrile copolymers, propylene-1-butene copolymers, propylene-isobutylene copolymers, styrenebutadiene copolymers and terpolymers such as, for example, those of ethylene, propylene and a diene such as hexadiene, dicyclopentadiene or ethylidenenorbornene, as well as terpolymers of acrylonitrile, styrene and butadiene; mixtures of the abovementioned homopolymers and copolymers, such as, for example, mixtures of polypropylene and polyethylene, polypropylene and polybutene-1, polypropylene and polyisobutylene, and polyacrylonitrile-styrene copolymers with polybutadiene.

The compounds of the formula I are incorporated in the substrates in a concentration of 0.01 to 5% by weight, calculated relative to the material to be stabilised. Preferably 0.05 to 1%, and particularly preferably 0.1 to 0.5% by weight of the compounds, relative to the material to be stabilised, are incorporated into the latter.

The incorporations of the new compounds into these polymers is for example effected, depending on the nature of the polymers, by incorporation of at least one of these compounds and optionally further additives into the melt in accordance with the methods customary in the art, before or during shaping, or by dissolving the polymer and the additives in solvents and subsequently evaporating the latter.

The new compounds can also be absorbed from baths, for example from aqueous dispersions or from solutions of organic solvents, onto polyolefine granules or onto polymeric carrier structures, such as films, filaments, split fibers, narrow tapes of films, or sheets.

In the case of crosslinked polyethylene the compounds are preferably added before crosslinking.

As further additives together with which the stabilisers usable according to the invention can be employed, there may be mentioned:

1. Antioxidants of the aminoaryl and hydroxyaryl series. In the case of the latter, the sterically hindered phenol compounds should be mentioned, for example: 2,2'-thiobis(4-methyl-6-tert.-butylphenol), 4,4'-thiobis-(3-methyl-6-tert.butylphenol), 2,2'-methylene-bis-(4-methyl-6-tert.-butylphenol), 2,2'-methylene-bis-(4-ethyl-6-tert.-butylphenol),-4,4'-methylene-bis-(2-methyl-6-tert.butylphenoyl), 4,4'-butylidene-bis-(3-methyl-6-tert.butylphenol), 2,2'-methylene-bis-[4-methyl-6-(α-methylcyclohexyl)-phenol], 2,6-di-(2-hydroxy-3-tert.butyl-5-methylbenzyl)-4-methyl-phenol, 2,6-di-tert.butyl-4-methylphenol, 1,1,3-tris-2-methyl-(4-hydroxy-5-tert.butyl-phenyl)-butane, 1,3,5-trimethyl-2,4,6-tri-(3,5-di-tert.butyl-4-hydroxybenzyl)-benzene, esters of β-4-hydroxy-3,5-di-tert.butylphenylpropionic acid with monohydric or polyhydric alcohols, such as methanol, ethanol, octadecanol, hexanediol, nonanediol, thiodiethylene glycol, trimethylolethane or pentaerythritol, 2,4-bis-octylmercapto-6-(4-hydroxy-3,5-di-tert.butylanilino)-s-triazine, 2,4-bis-(4-hydroxy-3,5-di-tert.butylphenoxy)-6-octylmercapto-s-triazine, 1,1-bis-(4-hydroxy-2-methyl-5-tert.butyl-phenyl)-3-dodecyl-mercapto-butane, 4-hydroxy-3,5-di-tert.butylbenzyl-phosphonic acid esters, such as the dimethyl, diethyl or dioctadecyl ester, (3-methyl-4-hydroxy-5-tert.butylbenzyl)-malonic acid dioctadecyl ester, s-(3,5-dimethyl-4-hydroxyphenyl)-thioglycollic acid octadecyl ester, and esters of bis-(3,5-di-tert.butyl-4-hydroxybenzyl)-malonic acid, such as the didodecyl ester, the dioctadecyl ester and 2-dodecylmercaptoethyl ester.

Amongst the aminoaryl derivatives, aniline and naphthylamine derivatives, as well as their heterocyclic derivatives, should be mentioned, for example phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl, and polymerised, 2,2,4-trimethyl-1,2-dihydroquinoline, though in the case of the combined use of the compounds of the formula I with the abovementioned amine compounds the stabilised polymer no longer possesses such good colour properties, because of the tendency to discoloration of the amine compounds.

2. UV-absorbers and other light protection agents such as:

a. 2-(2'-Hydroxyphenyl)-benztriazoles, for example the 5'-methyl, 3',5'-di-tert.butyl, 5'-tert.butyl, 5-chloro-3',5'-di-tert.butyl, 5-chloro-3'-tert.butyl-5'-methyl, 3',5'-di-tert.amyl, 3'-methyl-5'-β-carbomethoxyethyl, 5-chloro-3',5'-di-tert.amyl derivative.

b. 2,4-Bis-(2'-hydroxyphenyl)-6-alkyl-s-triazines, for example the 6-ethyl or 6-undecyl derivative.

c. 2-Hydroxy-benzophenones, for example the 4-hydroxy, 4-methoxy, 4-octoxy, 4-decyloxy, 4-dodecyloxy, 4,2',4'-trihydroxy or 2'-hydroxy-4,4'-dimethoxy derivative.

d. 1,3-Bis-(2'-hydroxy-benzoyl)-benzenes, for example 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

e. Acrylates, for example α-cyano-β,β-diphenylacrylic acid ethyl ester or isooctyl ester, α-carbomethoxy cinnamic acid methyl ester, α-cyano-β-methyl-p-methoxy-cinnamic acid methyl ester or butyl ester, and N-(β-carbomethoxy-vinyl)-2-methylindoline.

f. Nickel compounds, for example nickel complexes of 2,2'-thiobis-(4-tert.octylphenol), such as the 1:1- and 1:2-complex, optionally with other ligands such as n-butylamine, nickel complexes of bis-(4-tert.-octylphenyl)-sulphone, such as the 2:1 -complex, optionally with other ligands such as 2-ethylcaproic acid, nickel butyldithiocarbamate, nickel salts of 4-hydroxy-3,5-di-tert.butylbenzyl-phosphonic acid monoalkyl esters, such as of the methyl, ethyl or butyl ester, and the nickel complex of 2-hydroxy-4-methyl-phenyl-undecylketonoxime.

g. Oxalic acid diamides, for example 4,4'-di-octyloxyoxanilide, 2,2'-di-octyloxy-5,5'-di-tert.butyl-oxanilide and 2,2'-di-dodecyloxy-5,5'-di-tert.butyloxanilide.

3. Phosphites, such as triphenyl phosphite, diphenylalkyl phosphites, phenyldialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4 -hydroxy-3,5-di-tert.butylphenyl)-phosphite.

4. Nucleating agents, such as 4-tert.butylbenzoic acid, adipic acid and diphenylacetic acid.

5. Compounds which destroy peroxides, such as esters of β-thiodipropionic acid, for example the lauryl, stearyl, myristyl or tridecyl ester. Salts of 2-mercaptobenzimidazoles, for example the zinc salt and diphenylthiourea.

6. Other additives such as plasticisers, antistatic agents flameproofing agents, pigments, blowing agents, asbestos, glass fibers, kaolin and the talc.

When using the stabilisers according to the invention in combination with phenolic antioxidants, particularly good stabilising effects are achieved if compounds which destroy peroxides, such as higher alkyl esters of thiopropionic acid are employed simultaneously, since these compounds which destroy peroxides not only, as is known, show a synergism with the phenolic antioxidants, but additionally with the stabilisers of the formula I.

Particularly good stabilising effects are achieved with mixtures of 0.05 – 0.5% of a compound of the formula I and 0.1 – 0.8% of one of the UV-absorbers mentioned above under (a), (b), (c) and (d).

A further improvement of the stabilising effect can be achieved by ternary mixtures of 0.05 – 0.5% of a compound of the formula I, 0.1 – 0.8% of one of the UV-absorbers mentioned above under (a), (b), (c) and (d), and 0.1 – 0.1% of the nickel compounds mentioned above under (f).

The compounds according to the invention can be manufactured according to the following reaction which are in themselves known:

I. Acylation of a phenol with an appropriate acid chloride at room temperature, in the presence of a basic acceptor of hydrogen chloride.

II. Reaction of a phenol with an appropriate carboxylic acid in the presence of phosphorus oxychloride at temperatures of 50° – 120° C, preferably 80° – 100° C, optionally in the presence of an inert solvent.

The compounds can also be obtained by reaction of a phenol, in the form of a sodium or potassium salt, with an appropriate acid chloride in the presence of a solvent.

The invention is explained in more detail in the examples which follow.

EXAMPLE 1

34.9 g (0.13 mol) of 3,5-di-tert.butyl-4-hydroxybenzoyl chloride are introduced into a solution of 26.8 g (0.13 mol) of 2,4-di-tert.-butyl-o-cresol in 50 ml of dry pyridine, whilst stirring. After standing for 12 hours at room temperature, the reaction mixture is poured onto excess dilute hydrochloric acid, whilst cooling with ice, and the oil which has precipitated is extracted with methylene chloride. Extraction of the organic phase with dilute sodium carbonate solution and subsequent evaporation of the solvent yields the crude product as an oil. Recrystallisation from methanol yields 3,5-di-tert.-butyl-4-hydroxybenzoic acid 2'-methyl-4',6'-di-tert.-butylphenyl ester of melting point 173°–174° C, in the form of colourless crystals.

EXAMPLE 2

The procedure of Example 1 is followed, but the starting products are so chosen that the resulting aryl esters A – H correspond to the formulae listed in Table 1 below.

Table 1

| No. | Formula | Melting point [recrystallised from] |
|---|---|---|
| A | (3,5-di-t-C$_4$H$_9$-4-HO-C$_6$H$_2$)COO-(2,6-di-CH$_3$-4-t-C$_4$H$_9$-C$_6$H$_2$) | 1) 167–168° C  2) 183–184° C [methanol] |
| B | (3,5-di-t-C$_4$H$_9$-4-HO-C$_6$H$_2$)COO-(2-CH$_3$-4,6-di-t-C$_5$H$_{11}$-C$_6$H$_2$) | 144–145° C [methanol] |
| C | (3,5-di-t-C$_4$H$_9$-4-HO-C$_6$H$_2$)COO-(2,6-di-i-C$_3$H$_7$-4-t-C$_4$H$_9$-C$_6$H$_2$) | 147–149° C [methanol/water] |
| D | (3,5-di-t-C$_4$H$_9$-4-HO-C$_6$H$_2$)COO-(2,4,6-tri-i-C$_3$H$_7$-C$_6$H$_2$) | 145–146° C [ethanol/water] |

Table 1-continued

| No. | Formula | Melting point [recrystallised from] |
|---|---|---|
| E | t-C$_4$H$_9$, HO, t-C$_4$H$_9$ — benzene — COO — (2,6-dimethylphenyl) — h (phenyl) | 193–194° C [ethanol] |
| F | t-C$_4$H$_9$, HO, t-C$_4$H$_9$ — benzene — COO — (2,6-dimethylphenyl) — CH(CH$_3$)(C$_6$H$_5$) | 136–137° C [ethanol] |
| G | t-C$_4$H$_9$, HO, t-C$_4$H$_9$ — benzene — COO — (2,6-dimethylphenyl) — n-C$_{12}$H$_{25}$ | 59–60° C [methanol] |
| H | t-C$_4$H$_9$, HO, t-C$_4$H$_9$ — benzene — COO — (2,6-dimethylphenyl) | 113–114° C [methanol] |

EXAMPLE 3

A solution of 31.2 g (0.15 mol) of 3-methyl-5-tert.-butyl-4-hydroxybenzoic acid, 26.7 g (0.15 mol) of 4-tert.-butyl-2,6-xylenol and 7.70 g (0.05 mol) of phosphorus oxychloride in 60 ml of anhydrous benzene is boiled for 12 hours under reflux and subsequently decanted from a small amount of syrupy residue. After extracting the reaction solution with 5% strength aqueous sodium bicarbonate solution, drying over anhydrous sodium sulphate and evaporation of the solvent, the crude product is obtained as an oil. Recrystallisation from an ethanol/water mixture yields 3-methyl-5-tert.-butyl-4-hydroxybenzoic acid 4′-tert.-butyl-2′,6′-dimethylphenyl ester of melting point 207°–208° C, in the form of colourless crystals.

EXAMPLE 4

The procedure of Example 3 is followed, but the starting compounds are so chosen that the resulting aryl esters I - P correspond to the formulae listed in Table 2 below.

Table 2

| No. | Formula | Melting point [recrystallised from] |
|---|---|---|
| I | H$_3$C, HO, t-C$_4$H$_9$ — benzene — COO — (2,6-diisopropylphenyl) — t-C$_4$H$_9$ | 198–199° C [ethanol/water] |
| J | i-C$_3$H$_7$, HO, i-C$_3$H$_7$ — benzene — COO — (2,6-dimethylphenyl) — t-C$_4$H$_9$ | 226–228° C [ligroin] |

Table 2-continued

| No. | Formula | Melting point [recrystallised from] |
|---|---|---|
| K | (3,5-di-sec-butyl-4-hydroxybenzoic acid 2,4-dimethyl-... ester); structure: s-C₄H₉ and s-C₄H₉ on hydroxyphenyl (HO), COO-linked to phenyl with H₃C (ortho), CH₃ (ortho), CH₃ (para) | 162–163° C [isopropanol/water] |
| L | t-C₄H₉, t-C₄H₉ on HO-phenyl; COO linked to phenyl with s-C₄H₉ (ortho), Cl (ortho), s-C₄H₉ (para) | 121–122° C [ethanol] |
| M | t-C₄H₉, t-C₄H₉ on HO-phenyl; COO linked to phenyl with s-C₄H₉ (ortho), s-C₄H₉ (ortho), t-C₄H₉ (para) | 150–151° C [ethanol] |
| N | t-C₄H₉, t-C₄H₉ on HO-phenyl; COO linked to phenyl with H₃C (ortho), CH₃ (ortho), t-C₈H₁₇ (para) | 182–183° C [ligroin] |
| O | t-C₄H₉, t-C₄H₉ on HO-phenyl; COO linked to phenyl with H₃C (ortho), s-C₄H₉ (ortho), s-C₄H₉ (para) | 128–129° C [ethanol/water] |
| P | t-C₄H₉, t-C₄H₉ on HO-phenyl; COO linked to phenyl with s-C₄H₉ (ortho), s-C₄H₉ (ortho), s-C₄H₉ (para) | 111–112° C [ethanol/water] |

EXAMPLE 5

26.8 g [0.10 mol] of 3,5-di-tert.-butyl-4-hydroxybenzoyl chloride are added to a solution of 26.2 g [0.10 mol] of 2′,4′,6′-tri-tert.-butylphenol in 100 ml of toluene and the mixture is kept for 12 hours at 85° – 90° C. The hydrochloric acid gas thereby liberated is expelled from the reaction solution by passing dry nitrogen into the solution. After evaporation of the solvent, the crude product is recrystallised from methanol. 3,5-di-tert.-Butyl-4-hydroxybenzoic acid 2′,4′,6′-tri-tert.-butylphenyl ester of melting point 192°–93° C is obtained in the form of colourless crystals.

EXAMPLE 6

The procedure under Example 5 is followed, but the starting compounds are so chosen that the resulting aryl esters Q and R correspond to the formulae listed in Table 3 below.

Table 3

| No. | Formula | Melting point [recrystallised from] |
|---|---|---|
| Q | t-C$_4$H$_9$, COO-, s-C$_4$H$_9$, CH$_3$, CH$_3$, HO, t-C$_4$H$_9$ (3,5-di-tert-butyl-4-hydroxybenzoic acid 2',6'-dimethyl-4'-sec-butylphenyl ester) | 129–129.5° C [ethanol] |
| R | t-C$_4$H$_9$, COO-, s-C$_4$H$_9$, s-C$_4$H$_9$, HO, t-C$_4$H$_9$ | 121–122° C [ethanol] |

EXAMPLE 7

1000 parts of polypropylene powder [metl index 1.5 (230° C, 2160 g)] are mixed, in a drum mixer, with 1 part of β-(3,5-di-tert.-butyl-4-hydroxyphenyl)-propionic acid octadecyl ester and 2.5 parts of a light protection agent of Table 4 below, and subsequently granulated in a Buss Co-kneader at a temperature of 200° C.

The resulting granules are converted into a film in the usual manner, by means of an extruder and slit die; the film is cut into narrow tapes which are subsequently stretched hot, using a stretching ratio of 1:6, and wound up (gauge of the narrow tapes: 700 – 900 den, tensile strength: 5.5 – 6.5 g/den.).

The narrow polypropylene tapes thus manufactured are mounted on sample carriers, without tension, and are exposed to light in the Xeno 150 test apparatus. After various times, 5 test specimens at a time are removed and their tensile strength determined. The exposure time after which the tensile strength of the narrow tapes has declined to 30% of its value before exposure to light is treated as the measure of the protective action of the various light protection agents. The values obtained are listed in Table 4.

Table 4

| No. | Light protection agent | Hours of Xeno exposure till tensile strength drops to 30% of initial value |
|---|---|---|
| | None | 420 |
| | 3,5-di-tert.-butyl-4-hydroxy-benzoic acid dodecyl ester (comparison) | 1060 |
| | 3,5-di-tert.-butyl-4-hydroxy-benzoic acid 2',4'-di-tert.-butylphenyl ester (comparison) | 1400 |
| Example 1 | 3,5-di-tert.-butyl-4-hydroxy-benzoic acid 2'-methyl-4',6'-di-tert.-butylphenyl ester | 1420 |

EXAMPLE 8

1000 parts of polypropylene powder [melt index 20 (230° C, 2160 g)] are mixed in a Brabender Kneader with 2 parts of β-(3,5-di-tert.-butyl-4-hydroxyphenyl)-propionic acid octadecyl ester and 5 parts of a light protection agent from Table 5 below, at 200° C. The mixture homogenised in this way is withdrawn from the kneader and pre-pressed by means of a toggle press to give 2 – 3 mm thick sheets, which are subsequently converted in a heated platen press at 260° C, using suitable dies, firstly to 0.3 mm thick films and, in a further process stage, to 0.1 mm thick films.

The films manufactured in this way are annealed for 1 hour at 150° C whilst avoiding cooling below 150° C, and are immediately afterwards quenched in water at 15° C. The films manufactured in this way show a honogeneous, fine spherulitic structure. Test specimens punched therefrom show an elongation of approx. 900%.

The polypropylene films thus manufactured are mounted on sample carriers and exposed in the Xeno-150 test apparatus. After various times, pieces of film are removed, 5 test specimens at a time are punched, and their residual elongation is determined. The exposure time after which the elongation at break of the films has declined to 30% of its value before exposure to light is treated as a measure of the protective action of the individual light protection agents. The values obtained are listed in Table 5 below.

Table 5

| No. | Light protection agent | Hours of Xeno exposure till elongation at break drops to 30% of initial value |
|---|---|---|
| | None | 310 |
| | 3,5-di-tert.-butyl-4-hydroxy-benzoic acid dodecyl ester (comparison) | 1440 |
| | 3,5-di-tert.-butyl-4-hydroxy-benzoic acid 2',4'-di-tert.-butylphenyl ester (comparison) | 1800 |
| Example 1 | 3,5-di-tert.-butyl-4-hydroxy-benzoic acid 2'-methyl-4',6'-di-tert.-butylphenyl ester | 1810 |

EXAMPLE 9

1000 parts of polypropylene powder [melt index 1.5 (230° C, 2160 g)] are homogeneously mixed at 200° C in a Brabender Plastograph with 2 parts of β-(3,5-di-tert.-butyl-4-hydroxyphenyl)-propionic acid octadecyl ester and 5 parts of a light protection agent from Table 6 below, and the resulting composition is pressed in a platen press at 260° C to give 1 mm thick sheets. The sheets thus manufactured are exposed for 450 hours in the Xeno-150 test apparatus. The discoloration of the test specimens which thereby occurs is determined by measuring the Hunter values according to ASTM Standard Specification D 1365-55 and is compared with the values obtained on an unexposed sheet.

The results are listed in Table 6 below.

Table 6

| No. | Light protection agent | ΔE* |
|---|---|---|
|  | 3,5-di-tert.-butyl-4-hydroxy-benzoic acid 2',4'-di-tert.-butyl-phenyl ester (comparison) | 2.6 |
| Example 2C | 3,5-di-tert.-butyl-4-hydroxy-benzoic acid 4'-tert.-butyl-2',6'-di-i-propyl-phenyl ester | 1.1 |
| Example 2A | 3,5-di-tert.-butyl-4-hydroxy-benzoic acid 4'-tert.-butyl-2',6'-di-methyl-phenyl ester | 0.9 |

*ΔE = colour change (in NBS units) relative to the unexposed test specimen (NBS = National Bureau of Standards). A value of ΔE = 1 denotes that the sample exposed to light has not discoloured in any way relative to the unexposed sample.

EXAMPLE 10

1000 parts of polyethylene of density 0.917 are homogeneously mixed in a Brabender Plastograph at 200° C with 2 parts of β-(3,5-di-tert.-butyl-4-hydroxyphenyl)-propionic acid octadecyl ester and the light protection agents of Table 7, and the mixture is pressed into 1 mm thick sheets at 260° C. The sheets thus obtained are stored in air at room temperature and the degree of efflorescence of the additives is assessed visually after 5 days and 21 days. The results obtained are given in Table 7.

Table 7

| No. | Light protection agent | Visual assessment after | |
|---|---|---|---|
|  |  | 5 days | 21 days |
|  | 0.25% of 3,5-di-tert.-butyl-4-hydroxy-benzoic acid 2',4'-di-tert.-butylphenyl | strong efflorescence | — |
|  | 0.50% of 3,5-di-tert.-butyl-4-hydroxy-benzoic acid 2',4'-di-tert.-butylphenyl ester (comparison) | strong efflorescence | — |
| Example 4P | 0.25% of 3,5-di-tert.-butyl-4-hydroxy-benzoic acid 2',4',6'-tri-sec.-butyl-phenyl ester | fully compatible | fully compatible |
|  | 0.50% of 3,5-di-tert.-butyl-4-hydroxy-benzoic acid 2',4',6'-tri-sec.-butylphenyl ester | fully compatible | fully compatible |
| Example 2G | 0.25% of 3,5-di-tert.-butyl-4-hydroxy-benzoic acid 4'-n-dodecyl-2',6'-dimethyl-phenyl ester | fully compatible | fully compatible |
|  | 0.50% of 3,5-di-tert.-butyl-4-hydroxy-benzoic acid 4'-n-dodecyl-2',6'-dimethyl- | fully compatible | fully compatible |

I claim:

1. Compound of the formula I

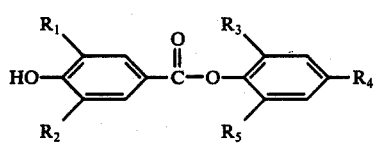

in which $R_1$ denotes alkyl with 1 to 5 carbon atoms, cycloalkyl with 5 to 8 carbon atoms or aralkyl with 7 to 9 carbon atoms, $R_2$ denotes α-branched alkyl with 3 to 8 carbon atoms, cycloalkyl with 5 to 8 carbon atoms or aralkyl with 7 to 9 carbon atoms, $R_3$ and $R_5$ independently of one another denote alkyl with 1 to 8 carbon atoms, cycloalkyl with 5 to 8 carbon atoms, aralkyl with 7 to 9 carbon atoms, phenyl or chlorine and $R_4$ denotes hydrogen, alkyl with 1 to 18 carbon atoms, cycloalkyl with 5 to 8 carbon atoms, aralkyl with 7 to 9 carbon atoms, phenyl or chlorine.

2. Compounds according to claim 1 of the formula I, in which $R_1$ denotes alkyl with 1 to 5 carbon atoms, $R_2$ denotes alkyl with 3 to 8 carbon atoms, with $R_1$ and $R_2$ together containing not more than 10 carbon atoms, $R_3$ and $R_5$ independently of one another denote alkyl with 1 to 8 carbon atoms, cycloalkyl with 6 to 8 carbon atoms, aralkyl with 7 or 8 carbon atoms or phenyl, and $R_4$ denotes hydrogen, alkyl with 1 to 12 carbon atoms, cycloalkyl with 6 to 8 carbon atoms, aralkyl with 7 – 8 carbon atoms, or phenyl.

3. Compounds according to claim 1 of the formula I, in which $R_1$ denotes alkyl with 1 to 4 carbon atoms, $R_2$ denotes alkyl with 3 and 4 carbon atoms, $R_3$ and $R_5$ independently of one another denote alkyl with 1 to 4 carbon atoms and $R_4$ denotes hydrogen, alkyl with 1 to 12 carbon atoms or cyclohexyl.

4. Compounds according to claim 1 of the formula I, in which $R_1$ denotes methyl, iso-propyl, sec.-butyl or tert.-butyl, $R_2$ denotes iso-propyl, sec.-butyl or tert.-butyl, $R_3$ and $R_5$ independently of one another denote methyl, iso-propyl, sec.-butyl, tert.-butyl, sec.-amyl, tert.-amyl, tert.-hexyl, tert.-octyl, cyclohexyl or α-methylbenzyl, and $R_4$ denotes hydrogen, methyl, iso-propyl, sec.-butyl, tert.-butyl, sec.-amyl tert.-amyl, tert.-hexyl, tert.-octyl, sec.-nonyl, tert.-dodecyl, cyclohexyl or α-methylbenzyl.

5. A compound according to claim 1 which is

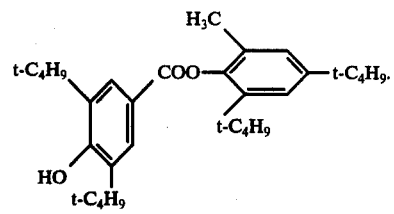

6. A compound according to claim 1 which is

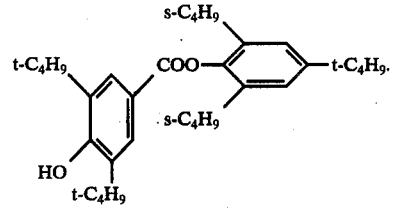

7. A compound according to claim 1 which is

8. A compound according to claim 1 which is
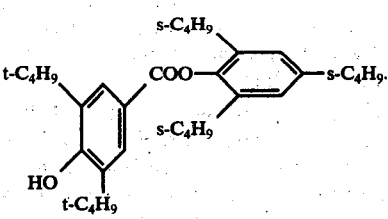
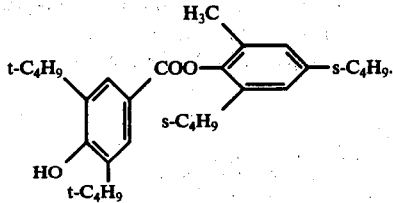
9. Composition comprising a compound of claim 1 and an organic polymer.
10. Composition according to claim 9, wherein the organic polymer is a polyolefine.
11. Composition according to claim 10, wherein the polyolefin is polypropylene.
12. Composition according to claim 10, wherein the polyolefin is polyethylene.
* * * * *